United States Patent
Stochniol et al.

(10) Patent No.: US 11,434,182 B2
(45) Date of Patent: Sep. 6, 2022

(54) PROCESS FOR THE OLIGOMERIZATION OF OLEFINS WITH CONTROL OF THE OLIGOMER CONTENT IN THE HYDROCARBON STREAMS TO BE OLIGOMERIZED

(71) Applicant: Evonik Operations GmbH, Essen (DE)

(72) Inventors: Guido Stochniol, Haltern am See (DE); Stephan Peitz, Oer-Erkenschwick (DE); Fabian Nadolny, Leipzig (DE); Benjamin William Berntsson, Duesseldorf (DE); Helene Reeker, Dortmund (DE); Reiner Bukohl, Marl (DE); Niklas Paul, Marl (DE)

(73) Assignee: Evonik Operations GmbH, Essen (DE)

( * ) Notice: Subject to any disclaimer, the term of this patent is extended or adjusted under 35 U.S.C. 154(b) by 158 days.

(21) Appl. No.: 15/929,604

(22) Filed: May 12, 2020

(65) Prior Publication Data

US 2020/0361835 A1 Nov. 19, 2020

(30) Foreign Application Priority Data

May 14, 2019 (EP) .................. 19174287

(51) Int. Cl.
*C07C 2/10* (2006.01)
*C07C 11/08* (2006.01)

(52) U.S. Cl.
CPC ............ *C07C 2/10* (2013.01); *C07C 11/08* (2013.01); *C07C 2523/755* (2013.01)

(58) Field of Classification Search
CPC ... C07C 2/10; C07C 2521/04; C07C 2521/08; C07C 2523/04; C07C 2523/755; C07C 2521/12; C07C 2/08; B01J 23/78; C10G 50/00
See application file for complete search history.

(56) References Cited

U.S. PATENT DOCUMENTS

| | | |
|---|---|---|
| 5,849,972 A | 12/1998 | Vicari et al. |
| 7,161,054 B2 | 1/2007 | Heidemann et al. |
| 2004/0181105 A1 | 9/2004 | Heidemann et al. |
| 2016/0152527 A1* | 6/2016 | Peitz ................ C07C 45/505 549/313 |

FOREIGN PATENT DOCUMENTS

| | | |
|---|---|---|
| DE | 4 339 713 | 5/2004 |
| EP | 1 457 475 A2 | 9/2004 |
| EP | 1 457 475 A3 | 9/2004 |
| WO | 2011/000697 | 1/2011 |

OTHER PUBLICATIONS

U.S. Appl. No. 15/929,599, filed May 12, 2020, Peitz et al.

* cited by examiner

*Primary Examiner* — Ali Z Fadhel
(74) *Attorney, Agent, or Firm* — Grüneberg and Myers PLLC

(57) ABSTRACT

A process for the oligomerization of $C_3$- to $C_5$-olefins proceeds in the presence of a catalyst, wherein the oligomerization is carried out in at least one reaction stage which includes at least one reactor and at least one distillation column. The content of oligomers in the feed stream to the at least one reaction stage after removal of the oligomers in the at least one distillation column is less than 0.4% by weight.

15 Claims, No Drawings

PROCESS FOR THE OLIGOMERIZATION OF OLEFINS WITH CONTROL OF THE OLIGOMER CONTENT IN THE HYDROCARBON STREAMS TO BE OLIGOMERIZED

CROSS-REFERENCE TO RELATED APPLICATION

The present application claims the benefit to European application EP 19174287.3, filed on May 14, 2019, the content of which is hereby incorporated by reference in its entirety.

BACKGROUND OF THE INVENTION

Field of the Invention

The present invention relates to a process for the oligomerization of $C_3$- to $C_5$-olefins using a catalyst, wherein the oligomerization is carried out in at least one reaction stage which comprises at least one reactor and at least one distillation column and wherein the content of oligomers in the feed stream to the at least one reaction stage after removal of the oligomers in the at least one distillation column is less than 0.4% by weight.

Discussion of the Background

Oligomerization is generally understood as meaning the reaction of unsaturated hydrocarbons with themselves to form correspondingly longer-chain hydrocarbons, the so-called oligomers. For instance, an olefin having six carbon atoms (hexene) can be formed by oligomerization of two olefins having three carbon atoms (propene). The oligomerization of two molecules with one another is also referred to as dimerization.

The resulting oligomers are intermediates that are used, for example, for producing aldehydes, carboxylic acids and alcohols. The oligomerization of olefins is carried out on a large industrial scale either in the homogeneous phase using a dissolved catalyst or heterogeneously over a solid catalyst, or else with a biphasic catalyst system.

Processes for oligomerizing olefins are sufficiently well known in the related art and are used on an industrial scale. The production quantities amount to several thousand kilotons per year in Germany alone. The source of the olefins for the oligomerization processes are generally olefin-containing fractions from cracking processes (for example steam crackers or fluid catalytic crackers) which, in addition to the olefins, also comprise corresponding alkanes.

After producing the olefin oligomers in one or more reactors connected in series, the oligomers must be separated from the oligomerizate (output from the oligomerization), which comprises, inter alia, unreacted feed olefins and/or alkanes. The separation is typically carried out in at least one distillation column, wherein the unreacted olefins and/or the alkanes leave via the overhead and are at least partially recycled to the reactor(s).

The aim of the separation of the oligomers from the oligomerizate is usually to produce a pure oligomerizate without fractions of starting material and a pure stream of unreacted feed olefins and/or alkanes, which are then reused accordingly. However, the problem is that with purity of the said streams to be increased, the costs for the separating apparatus(es) and/or the energy costs, for example due to the necessity for an increased column return, are significantly higher. To reduce costs, the oligomers are therefore usually not separated off in pure form, but rather small amounts of starting materials remain in the separated oligomer stream. The same applies to the stream of unreacted feed olefins and/or alkanes which still comprise certain amounts of oligomers even after separation.

If these streams of feed olefins and/or alkanes and also the oligomers are fed back to the reactor, it is noticeable that on the one hand the oligomer yield drops and on the other hand the reaction rate in the oligomerization decreases the higher the proportion of oligomers returned. There is, therefore, a certain inhibition of oligomerization that has to be taken into account.

The object of the present invention was therefore to provide a process for the oligomerization of $C_3$- to $C_5$-olefins in which no significant drop in the reaction rate, i.e. no noticeable inhibition, can be observed, and nevertheless a cost-effective separation effect can be achieved.

SUMMARY OF THE INVENTION

The present invention includes the following embodiments:

1. Process for the oligomerization of $C_3$- to $C_5$-olefins, wherein a feed mixture comprising the $C_3$- to $C_5$-olefins is oligomerized in at least one reaction stage using a heterogeneous oligomerization catalyst comprising a nickel compound and a support material, containing aluminum oxide, silicon dioxide or aluminosilicate, wherein one reaction stage in each case consists of at least one reactor in which the oligomerization is carried out forming an oligomerizate, and at least one distillation column in which the oligomers formed during the oligomerization are at least partially separated from the residual oligomerizate, characterized in that at least a portion of the residual oligomerizate from which the oligomers have been separated is recycled to one or more reactor(s) of the at least one reaction stage and the content of oligomers in the feed to one or more reactor(s) of the at least one reaction stage, which consists of the recycled residual oligomerizate and the fresh feed of the feed mixture, is less than 0.4% by weight, based on the total composition of the feed.

Process according to embodiment 1, wherein the content of oligomers in the feed to one or more reactor(s) of the at least one reaction stage is ≤0.2% by weight, based on the total composition of the feed.

3. Process according to embodiment 1 or 2, wherein the process for oligomerization is carried out in at least two reaction stages, wherein the oligomers formed in the reactor or in the reactors of the first reaction stage are separated from the residual oligomerizate in the distillation column of the first reaction stage and wherein the residual oligomerizate is fed partly to the reactor(s) of the same reaction stage and partly to the reactor(s) of the next reaction stage.

4. Process according to any of embodiments 1 to 3, wherein the support material of the oligomerization catalyst comprises an aluminosilicate.

5. Process according to embodiment 4, wherein the support material of the oligomerization catalyst consists of an aluminosilicate.

6. Process according to embodiment 4 or 5, wherein the heterogeneous oligomerization catalyst has a composition of 15 to 40% by weight NiO, 5 to 30% by weight $Al_2O_3$, 55 to 80% by weight $SiO_2$ and 0.01 to 2.5% by weight of an alkali metal oxide.

7. Process according to any of embodiments 1 to 6, wherein the oligomerization catalyst has a specific surface, calculated according to BET, of 150 to 700 m²/g.

8. Process according to any of embodiments 1 to 7, wherein the oligomerization in each of the reaction stages present is carried out at a temperature in the range of 50 to 200° C., preferably 60 to 180° C., particularly preferably in the range of 60 to 130° C.

9. Process according to any of embodiments 1 to 8, wherein the pressure in the oligomerization in each of the reaction stages present is 10 to 70 bar, preferably 20 to 55 bar.

10. Process according to any of embodiments 1 to 9, wherein the process is a process for oligomerizing $C_4$-olefins.

11. Process according to any of embodiments 1 to 10, wherein the oligomerization in each of the at least one reaction stages is carried out in the liquid phase.

12. Process according to any of embodiments 1 to 11, wherein the degree of dimerization after the oligomerization is at least 60% based on the converted reactant.

13. Process according to any of embodiments 1 to 12, wherein the weight hourly space velocity (WHSV) during the oligomerization is from 1 g of reactant per g of catalyst and per h, i.e. 1 h$^{-1}$ to 190 h$^{-1}$.

DETAILED DESCRIPTION OF THE INVENTION

It has been found that the negative effects described (decrease in oligomer yield and reaction rate) occur precisely when the oligomers are not adequately removed from the stream of unreacted feed olefins and/or the alkanes. The underlying object could therefore be achieved in accordance with the invention in that the content of oligomers in the feed stream to the reactor or reactors of at least one reaction stage is less than 0.4% by weight, based on the total composition of the feed to the reactor or reactors of the at least one reaction stage. The feed consists of recycled residual oligomerizate, from which the oligomers formed have been removed by distillation, and the fresh feed of the feed mixture. This is reproduced in a preferred embodiment. Further embodiments of the process are specified below.

The process according to the invention is thus a process for the oligomerization of $C_3$- to $C_5$-olefins, preferably $C_4$-olefins, wherein a feed mixture comprising the $C_3$- to $C_5$-olefins, preferably the $C_4$-olefins, is oligomerized in at least one reaction stage using a heterogeneous oligomerization catalyst comprising a nickel compound and a support material, containing aluminum oxide, silicon dioxide or aluminosilicate, wherein a reaction stage in each case consists of at least one reactor in which the oligomerization is carried out forming an oligomerizate, and at least one distillation column in which the oligomers formed during the oligomerization are at least partially separated from the residual oligomerizate, wherein at least part of the residual oligomerizate from which the oligomers have been separated is recycled to one or more reactor(s) of the at least one reaction stage and the content of oligomers in the feed to one or more reactor(s) of the at least one reaction stage, which consists of the recycled residual oligomerizate and fresh feed of the feed mixture, is less than 0.4% by weight, preferably ≤0.2% by weight, based in each case on the total composition of the feed.

The content of oligomers can also be monitored, for example using gas chromatographic methods, during ongoing operation. In order to be able to achieve a sufficient separation between oligomers and residual oligomerizate and thus an oligomer content in the feed of less than 0.4% by weight, preferably ≤0.2% by weight, various measures can be taken individually or in combination, for example the use of one or more larger distillation columns, better packings in the distillation column(s), less load on the distillation column(s) or an increased distillate return to the distillation column(s). In addition, the oligomer contents according to the invention can also be achieved by adjusting the ratio of the recycled residual oligomerizate to the fresh feed (recycled residual oligomerizate/fresh feed). In principle, oligomer contents of less than 0.4% by weight, preferably ≤0.2% by weight, can also be achieved in that the amount of recycled residual oligomerizate is low. In a preferred embodiment, the ratio of recycled residual oligomerizate (in t/h) and fresh feed (in t/h) is 0.001 to 30, preferably 0.005 to 20 and particularly preferably 0.01 to 15.

In the context of the present invention, the term "reaction stage" means a plant section comprising one or more reactor(s) and one or more distillation column(s) downstream of the reactor. In a preferred embodiment, only one distillation column is present per reaction stage. In the distillation columns, the oligomers formed are separated from the oligomerizate (which corresponds to the output stream from the reactor), which in addition to the oligomers also comprises alkanes and unreacted olefins. Typical process-engineering units which can be incorporated in the reaction stages, such as preheaters for the feed, heat exchangers or similar, for example, are not listed separately here but are familiar to those skilled in the art.

The process according to the invention comprises at least one reaction stage. However, the process can also comprise at least two reaction stages, preferably not more than five reaction stages. In a preferred embodiment, the process for the oligomerization therefore comprises two, three, four or five reaction stages. Each of these reaction stages, independently of one another, comprises one or more reactors and one or more downstream distillation columns in order to separate the oligomers formed from the residual output stream from the reactor. It is also conceivable, however, that one of the reaction stages comprises two or more reactors, whereas in a preceding or subsequent reaction stage only one reactor is present.

In the single-stage process regime with only one reaction stage, the oligomers formed in the reactor or in the reactors of the first reaction stage are separated from the residual oligomerizate in the distillation column of the first reaction stage such that the oligomer content in the total feed to the reactor or the reactors is less than 0.4% by weight, preferably ≤0.2% by weight, if the residual oligomerizate is at least partially mixed with fresh feed and fed to the reactor(s) of the reaction stage. In the case of the process regime with two or more reaction stages, the content of oligomers in the feed stream for all reactors of all reaction stages is less than 0.4% by weight, preferably ≤0.2% by weight. In the case of the process regime with two or more reaction stages, the residual oligomerizate, from which the oligomers have been separated in the distillation column, can be partly fed to the, or to one of, the reactor(s) of the same reaction stage and partly to the next reaction stage. The at least partial conveying of the residual oligomerizate to the next reaction stage is naturally not applicable in the last reaction stage. In addition to recycling to the reactor of the same reaction stage and conveying to the next reaction stage, part of the residual oligomerizate can also be removed, for example to prevent inert alkanes from accumulating in the system.

The process according to the invention can be carried out broadly as follows: the starting point is the provision of a feed mixture comprising $C_3$- to $C_5$-olefins, preferably $C_4$-olefins. The feed mixture is firstly oligomerized in the at least one reactor of the first reaction stage and the oligomerizate obtained is passed to a distillation column in which the oligomers formed (preferably $C_6$- to $C_{24}$-olefins, particularly preferably $C_8$- to $C_{24}$-olefins) are separated as bottom product from the residual oligomerizate, which comprises at least unreacted olefins and alkanes from the feed mixture and which is obtained as the overhead product. Depending on the reaction stage, the residual oligomerizate is then at least partially passed as a feed stream to the next respective reaction stage and partially recycled to the reactor of the same reaction stage and beforehand combined with fresh feed composed of fresh feed mixture or with the oligomer-depleted oligomerizate of the previous stage. In the last reaction stage, the residual oligomerizate, after the oligomers have been separated off, is partially recycled to one of the reactors and at least partially discharged from the process. If the residual oligomerizate of the last reaction stage is discharged from the process described here, this can serve as synthetic raw material for further processes (e.g. hydroformylation, C-source for light arc in acetylene production), as combustion gas or as a propellant gas after full hydrogenation to alkanes, as cooking gas and the like.

Olefins employable for the process according to the invention are $C_3$- to $C_5$-olefins, preferably $C_4$-olefins or olefin mixtures based thereon, which may also comprise proportions of analogous alkanes. Suitable olefins include α-olefins, n-olefins and cycloalkenes, preferably n-olefins. In a preferred embodiment, the $C_4$-olefin is n-butene.

The olefins are typically not used as reactants in pure form, but in available technical-grade mixtures. The term feed mixture used in this invention is therefore to be understood as encompassing any type of mixture containing the relevant olefins to be oligomerized in an amount which makes it possible to perform the oligomerization economically. The feed mixtures used in accordance with the invention preferably contain practically no further unsaturated compounds and polyunsaturated compounds such as dienes or acetylene derivatives. It is preferable to employ feed mixtures containing less than 5% by weight, in particular less than 2% by weight, of branched olefins based on the olefin proportion.

Propylene is produced on a large industrial scale by cracking of naphtha and is a commodity chemical which is readily available. $C_5$-olefins are present in light petroleum fractions from refineries or crackers. Technical mixtures which comprise linear $C_4$-olefins are light petroleum fractions from refineries, $C_4$-fractions from FC crackers or steam crackers, mixtures from Fischer-Tropsch syntheses, mixtures from the dehydrogenation of butanes, and mixtures formed by metathesis or from other industrial processes. Mixtures of linear butenes suitable for the process according to the invention are obtainable for example from the C$_4$-fraction of a steam cracker. Butadiene is removed in the first step here. This is accomplished either by extraction (distillation) of the butadiene or by selective hydrogenation thereof. In both cases a virtually butadiene-free $C_4$-cut is obtained, the so-called raffinate I. In the second step, isobutene is removed from the $C_4$-stream, for example by production of MTBE by reaction with methanol. The now isobutene-free and butadiene-free $C_4$-cut, the so-called raffinate ii, contains the linear butenes and any butanes. If at least some of the 1-butene obtained is removed therefrom, the so-called raffinate III is obtained.

In a preferred embodiment in the process according to the invention, $C_4$-olefin-containing streams are fed as feed mixture. Suitable substance streams containing $C_4$-olefin are in particular raffinate I, raffinate II and raffinate III.

All reactors known to those skilled in the art can be used as reactor for the respective reaction stages which are suitable for oligomerization, for example tubular reactors, tube bundle reactors, settler-riser reactors, slurry reactors. Preference is given to tubular reactors and/or tube bundle reactors. If a reaction stage has two or more reactors, the reactors can be the same or different from one another. The reactors in a reaction stage may also vary in their construction or their configuration. The first reactor in a reaction stage may have, for example, a larger volume than the subsequent reactor in the same reaction stage. It is also possible that the reactors in the individual reaction stages, provided there are two or more reaction stages, are the same or different from one another. It is also possible here that the reactors in the individual reaction stages are different in their construction or their configuration. The reactor in the first reaction stage may have, for example, a larger volume than one or all reactors in the downstream reaction stages.

The one reactor or the reactors of the individual reaction stages contain in each case an oligomerization catalyst for carrying out the oligomerization, especially a heterogeneous oligomerization catalyst. The oligomerization catalyst in this case is particularly in the form of granules, an extrudate or in tablet form.

The (heterogeneous) oligomerization catalysts in the individual reactors of the reaction stages can each be selected independently of one another from transition metal-containing oligomerization catalysts. The transition metals or the appropriate transition metal compounds used are preferably arranged on a support material, containing aluminum oxide, silicon dioxide or aluminosilicate, preferably an aluminosilicate support material. Compounds of nickel, cobalt, chromium, titanium and tantalum are particularly suitable as transition metal compounds for the oligomerization catalysts used according to the invention. Preference is given to nickel and cobalt compounds, particular preference being given to nickel compounds.

According to the present invention, the oligomerization catalyst according to the invention comprises a nickel compound, preferably nickel oxide, and a support material containing or consisting of aluminum oxide, silicon dioxide or aluminosilicate, preferably aluminosilicate. The support material is preferably an X-ray amorphous mesoporous aluminosilicate, a crystalline microporous aluminosilicate or an aluminosilicate which has amorphous and crystalline phases. In the context of the present invention, "amorphous" is to be understood as meaning the property of a solid which results from the fact that the solid has no crystal structure, i.e. no long-range order. In the context of the present invention, however, it cannot be ruled out that the amorphous aluminosilicate has small crystalline domains.

Further preferred in accordance with the invention, the oligomerization catalyst has a composition of 15% to 40% by weight, preferably 15% to 30% by weight NiO, 5% to 30% by weight $Al_2O_3$, 55% to 80% by weight $SiO_2$ and 0.01% to 2.5% by weight, preferably 0.05% to 2% by weight, of an alkali metal oxide, preferably sodium oxide. The figures are based on a total composition of 100% by weight. In a particularly preferred embodiment of the present invention, the oligomerization catalyst is substantially free from titanium dioxide and/or zirconium dioxide, the oligomerization catalyst in particular comprising less than 0.5% by weight, preferably less than 0.1% by weight, particularly preferably less than 0.01% by weight, of titanium dioxide and/or zirconium dioxide in its total composition.

The oligomerization catalyst preferably has a specific surface area (calculated according to BET) of 150 to 700 m²/g, more preferably 190 to 600 m²/g, particularly preferably 220 to 550 m²/g. The BET surface area is measured by nitrogen physisorption according to DIN ISO 9277 (2014-01 version).

If there are two or more reactors in one reaction stage or in two or more reaction stages, there are naturally also two or more oligomerization catalysts. The oligomerization catalysts present in the individual reactors in the reaction stages may be selected in each case independently of one another from the aforementioned substances. The individual oligomerization catalysts in the reactors are not always exactly identical here, but differ from each other in the composition, possibly only to a limited extent. This is also due to the fact that even if each reactor contains a completely identical catalyst composition at the time when the process according to the invention is first started up, this composition changes during operation over time as a result of various effects over the years.

An oligomerization catalyst can be produced by the known processes of impregnation, wherein the support material is charged with a solution of a transition metal compound, especially a nickel compound, and is then calcined, or coprecipitation in which the entire catalyst composition is precipitated from a single, mostly aqueous solution. The oligomerization catalyst can also be produced by other processes familiar to those skilled in the art.

The oligomerization can be carried out in each of the reaction stages present at a temperature in the range of 50 to 200° C., preferably 60 to 180° C., preferably in the range of 60 to 130° C., The pressure of each of the reaction stages present can be from 10 to 70 bar, preferably 20 to 55 bar. In a preferred embodiment of the present invention, the oligomerization is carried out in each reaction stage in the liquid phase. If the oligomerization is to be carried out in the liquid phase the parameters pressure and temperature must to this end be chosen such that the reactant stream (the employed olefins or olefin mixtures) is in the liquid phase.

The weight-based space velocities (reactant mass per unit catalyst mass per unit time; weight hourly space velocity (WHSV)) are in the range between 1 g of reactant per g of catalyst and per h (i.e. 1 h⁻¹) and 190 h⁻¹, preferably between 2 h⁻¹ and 35 h⁻¹, particularly preferably between 3 h⁻¹ and 25 h⁻¹.

Particularly when using a catalyst comprising a nickel compound, preferably nickel oxide, on a support material, the degree of dimerization (also referred to as "percentage selectivity based on dimerization") after the oligomerization, based on the converted reactant, is at least 60%, more preferably at least 75%, particularly preferably at least 80%.

The linearity of an oligomerization product or of the dimers formed is described by the ISO index and represents a value for the average number of methyl branches in the dimer. For example (for butene as the reactant), n-octenes contribute 0, methylheptenes contribute 1 and dimethylhexenes contribute 2 to the ISO index of a $C_8$ fraction. The lower the ISO index, the more linear the construction of the molecules in the respective fraction. The ISO index is calculated according to the following general formula, wherein the proportion of the individual dimer fractions refers to the total dimer fraction:

$$\frac{\left(\begin{array}{c}\text{single-}branched\text{ dimer (wt \%) +}\\ 2\times\text{double-}branched\text{ dimer (wt \%)}\end{array}\right)}{100}$$

Accordingly, a dimer mixture having an ISO index of 1.0 has an average of exactly 1 methyl branch per dimeric molecule.

The ISO index of the product from the oligomerization process according to e invention is preferably 0.8 to 1.2, more preferably 0.8 to 1.15.

The oligomers produced by the process according to the invention are utilized inter alia for producing aldehydes, alcohols and carboxylic acids. Thus for example the dimerizate of linear butenes affords a nonanal mixture by hydroformylation. This provides either the corresponding carboxylic acids by oxidation or a $C_9$-alcohol mixture by hydrogenation. The $C_9$-acid mixture may be used for producing lubricants or siccatives. The $C_9$-alcohol mixture is a precursor for the production of plasticizers, particularly dinonyl phthalates, or DINCH.

EXAMPLES

Example 1 (Inventive)

The oligomerization was reworked in a substantially isothermal tubular reactor with the following dimensions: length 2.0 m, internal diameter 6 mm. The reactor was suspended in a thermostat for thermostatting. The heat carrier used was the Marlotherm product from Sasol. The catalyst used was 12.6 g of a material which had been prepared in accordance with example 1 of WO2011/000697A1 and had been post-treated in accordance with example 4 of the same publication.

The reaction was carried out at an absolute pressure of 30 bar and a temperature of 80° C. in the liquid phase. 1 kg/h of a $C_4$-hydrocarbon mixture containing the following components was used as fresh feed to the reactor:

1-butene 22.7% by weight
2-butene 58.4% by weight
isobutene 0.7% by weight
butanes 18.1% by weight
$C_8$-olefins 0.1% by weight A conversion of $C_4$ olefins of 43.9% was achieved, the following oligomerizate distribution being achieved in the reactor discharge:

$C_8$-olefins 83.9%
$C_{12}$-olefins 12.5%
$C_{16+}$-olefins 3.7%

This corresponds to a product amount of 34.4 g/h of $C_8$-olefins.

Example 2 (Non-Inventive)

The oligomerization was reworked in a substantially isothermal tubular reactor with the following dimensions: length 2.0 m, internal diameter 6 mm. The reactor was suspended in a thermostat for thermostatting. The heat carrier used was the Marlotherm product from Sasol. The catalyst used was 12.6 g of a material which had been prepared in accordance with example 1 of WO2011/000697A1 and had been post-treated in accordance with example 4 of the same publication.

The reaction was carried out at an absolute pressure of 30 bar and a temperature of 80° C. in the liquid phase. 1 kg/h of a $C_4$-hydrocarbon mixture containing the following components was used as fresh feed to the reactor:

1-butene 22.2% by weight
2-butene 57.9% by weight
isobutene 0.6% by weight
butanes 18.2% by weight
$C_8$-olefins 1.1% by weight A conversion of $C_4$-olefins of 41.1% was achieved, the following oligomerizate distribution being achieved in the reactor discharge:

$C_8$-olefins 83.9%
$C_{12}$-olefins 12.4%
$C_{16+}$-olefins 3.8%

This corresponds to a product amount of 32.0 g/h of $C_8$-olefins.

It could be shown that an increase in the $C_8$-olefin content in the feed to the reactor leads to a decrease in conversion by 2.8 percentage points and to a reduction in the amount of $C_8$-oligomers produced of 7%.

Example 3 (Inventive)

The oligomerization was reworked in a substantially adiabatic tubular reactor without thermostatting with the following dimensions: length 2.0 m, internal diameter 20.5 mm. The catalyst used was 300 g of a material which had been prepared in accordance with example 1 of WO2011/000697A1 and had been post-treated in accordance with example 4 of the same publication.

The reaction was carried out at an absolute pressure of 30 bar and a reactor feed temperature of 90° C. in the liquid phase. 1.75 kg/h of a $C_4$-hydrocarbon mixture containing the following components was used as fresh feed to the reactor:

1-butene 35.8% by weight
2-butene 42.4% by weight
isobutene 0.9% by weight
butanes 20.9% by weight
$C_8$-olefins 0.0% by weight A conversion of $C_4$-olefins of 31.7% was achieved, the following oligomerizate distribution being achieved in the reactor discharge:

$C_8$-olefins 85.1%
$C_{12}$-olefins 12.6%
$C_{16+}$-olefins 2.3%

Example 4 (Inventive)

The conditions and the reactor corresponded to those of example 3. A $C_4$ mixture was used that had the following composition:

1-butene 36.0% by weight
2-butene 43.8% by weight
isobutene 0.7% by weight
butanes 19.3% by weight
$C_8$-olefins 0.2% by weight (corresponds to 3.5 g/h)

A conversion of $C_4$-olefins of 31.7% was achieved, the following oligomerizate distribution being achieved in the reactor discharge:

$C_8$-olefins 85.0%
$C_{12}$-olefins 12.6%
$C_{16}$+-olefins 2.4%

No decrease in conversion compared to example 3 could be determined.

Example 5 (Non-Inventive)

The conditions and the reactor corresponded to those of example 3. A $C_4$ mixture was used that had the following composition:

1-butene 36.1% by weight
2-butene 44.1% by weight
isobutene 1.2% by weight
butanes 18.0% by weight
$C_8$-olefins 0.4% by weight (corresponds to 7 g/h)

A conversion of $C_4$-olefins of 30.1% was achieved, the following oligomerizate distribution being achieved in the reactor discharge:

$C_8$-olefins 85.0%
$C_{12}$-olefins 12.6%
$C_{16+}$-olefins 2.4%

A slighter decrease in conversion compared to Example 3 was observed.

Example 6 (Non-Inventive)

The conditions and the reactor corresponded to those of example 3. A $C_4$ mixture was used that had the following composition:

1-butene 34.3% by weight
2-butene 44.1% by weight
isobutene 1.1% by weight
butanes 19.9% by weight
$C_8$-olefins 0.7% by weight (corresponds to 12 g/h)

A conversion of $C_4$-olefins of 28.8% was achieved, the following oligomerizate distribution being achieved in the reactor discharge:

$C_8$-olefins 85.1%
$C_{12}$-olefins 12.6%
$C_{16+}$-olefins 2.3%

The invention claimed is:

1. A process for oligomerization of $C_3$- to $C_5$-olefins, comprising:
    oligomerizing a feed mixture comprising the $C_3$- to $C_5$-olefins in at least one reaction stage and in the presence of a heterogeneous oligomerization catalyst comprising
        a nickel compound, and
        a support material, comprising
            an aluminum oxide, a silicon dioxide, or an aluminosilicate,
    wherein one reaction stage in each case comprises
        at least one reactor in which the oligomerization is carried out forming an oligomerizate, and
        at least one distillation column in which the oligomers formed during the oligomerization are at least partially separated from a residual oligomenzate,
    wherein at least a portion of the residual oligomerizate from which the oligomers have been separated is recycled to one or more reactor(s) of the at least one reaction stage, and a content of oligomers in a feed to one or more reactor(s) of the at least one reaction stage, which comprises the recycled residual oligomerizate and a fresh feed of the feed mixture, is less than 0.4% by weight, based on a total composition of the feed,
    wherein a content of oligomers is monitored during ongoing operation.

2. The process according to claim 1, wherein the content of oligomers in the feed to one or more reactor(s) of the at least one reaction stage is ≤0.2% by weight, based on the total composition of the feed.

3. The process according to claim 1, wherein the oligomerization is carried out in at least two reaction stages, wherein the oligomers formed in the reactor or in the reactors of the first reaction stage are separated from the residual oligomerizate in the distillation column of the first reaction stage, and wherein the residual oligomerizate is fed partly to the reactor(s) of the same reaction stage and partly to the reactor(s) of the next reaction stage.

4. The process according to claim 1, wherein the support material of the oligomerization catalyst comprises the aluminosilicate.

5. The process according to claim 4, wherein the support material of the oligomerization catalyst consists of the aluminosilicate.

6. The process according to claim 4, wherein the heterogeneous oligomerization catalyst has a composition of:
15 to 40% by weight NiO,
5 to 30% by weight $Al_2O_3$,
55 to 80% by weight $SiO_2$, and
0.01 to 2.5% by weight of an alkali metal oxide.

7. The process according to claim 1, wherein the oligomerization catalyst has a specific surface area, calculated according to BET, of 150 to 700 $m^2/g$.

8. The process according to claim 1, wherein the oligomerization in each of the reaction stages present is carried out at a temperature in the range of 50 to 200° C.

9. The process according to claim 1, wherein a pressure in the oligomerization in each of the reaction stages present is 10 to 70 bar.

10. The process according to claim 1, wherein the process is a process for oligomerizing $C_4$-olefins.

11. The process according to claim 1, wherein the oligomerization in each of the at least one reaction stages is carried out in a liquid phase.

12. The process according to claim 1, wherein a degree of dimerization after the oligomerization is at least 60% based on a converted reactant.

13. The process according to claim 1, wherein weight hourly space velocity (WHSV) during the oligomerization is from 1 g of reactant per g of catalyst and per h: 1 $h^{-1}$ to 190 $h^{-1}$.

14. The process according to claim 8, wherein the temperature is in the range of 60 to 130° C.

15. The process according to claim 9, wherein the pressure is from 20 to 55 bar.

* * * * *